US009629887B1

(12) United States Patent
Lasneski et al.

(10) Patent No.: US 9,629,887 B1
(45) Date of Patent: Apr. 25, 2017

(54) CONTROL OF ACID REFLUX WITH BOTANICALS

(71) Applicants: Gary Lasneski, Suffield, CT (US); William S. Sparks, Bellaire, TX (US); Daryl L. De Luca, Sugar Land, TX (US); Denis R. De Luca, Fulshear, TX (US)

(72) Inventors: Gary Lasneski, Suffield, CT (US); William S. Sparks, Bellaire, TX (US); Daryl L. De Luca, Sugar Land, TX (US); Denis R. De Luca, Fulshear, TX (US)

(73) Assignee: Biotics Research Corporation, Rosenberg, TX (US)

( * ) Notice: Subject to any disclaimer, the term of this patent is extended or adjusted under 35 U.S.C. 154(b) by 138 days.

(21) Appl. No.: 14/298,414

(22) Filed: Jun. 6, 2014

(51) Int. Cl.
*A61K 38/46* (2006.01)
*A61K 36/73* (2006.01)
*A61K 36/185* (2006.01)
*A61K 36/64* (2006.01)
*A61K 36/68* (2006.01)
*A61K 38/48* (2006.01)

(52) U.S. Cl.
CPC ............ *A61K 36/73* (2013.01); *A61K 36/185* (2013.01); *A61K 36/64* (2013.01); *A61K 36/68* (2013.01); *A61K 38/488* (2013.01)

(58) Field of Classification Search
CPC ...... A61K 36/73; A61K 36/185; A61K 36/64; A61K 36/68; A61K 38/488
See application file for complete search history.

(56) References Cited

U.S. PATENT DOCUMENTS

| | | | |
|---|---|---|---|
| 2006/0257351 A1* | 11/2006 | Chiba .................... | A61K 8/347 424/74 |
| 2009/0004302 A1* | 1/2009 | Cyr ....................... | A23L 1/3002 424/732 |
| 2009/0110674 A1* | 4/2009 | Loizou .................. | A61K 36/00 424/94.2 |

OTHER PUBLICATIONS

Olivier R., Specific botanicals as an aid for acid reflux, Published on the web on Jan. 9, 2014 at http://www.tuesdayminute.net/Specific%20Botanicals%20As%20An%20Aid%20For%20Acid%20Reflux-Dr.%20Olivier.pdf; published in paper, Jun. 2014 in The Original Internist, pp. 85,86 and 88.*
Vita Logic—A Brochure on Stomach Formula (a commercial preparation of herbal supplement), published on web on Jan. 14, 2008; at http://www.luckyvitamin.com/images/brochures/Vita_Logic_Stomach_Formula.pdf, pp. 1-2.*
Andoh, Tsugunobu et al, Effects of Goshajinkigan, Hachimijiogan, and Rokumigan on Mechanical Allodynia Induced by Paclitaxel in Mice, Journal of Traditional and Complementary Medicine Vol. 4, No. 4, pp. 293-297 (2014) Committee on Chinese Medicine and Pharmacy, Taiwan.
WEBMD, What is Acid Reflux Disease, web page, http://webmd.com/heartburn-gerd/guide/what-is-acid-reflux-disease (2014).
Clare, Dilis, Dr., Dr. Clare's Academy of Herbal Medicine, Meadowsweet Filipendula, http://drclaresacademy.com/mod/glossary/showentry.php?courseid=1&eid=31&displayformat=dictionary (2015) citing Schultz 1998 and McGuffin 1997.
Newall CA, Anderson LA, Philpson JD. Herbal Medicine: A Guide for Healthcare Professionals. London, UK: The Pharmaceutical Press, 1996 p. 191.
Blumenthal M, Busse WR, Goldberg A, Gruenwald J, Hall T, Riggins CW, Rister RS. The Complete German Commission E Monographs. Therapeutic Guide to Herbal Medicines. Am Botanical Council. Austin, TX 1998 p. 169.
Rxlist Inc., Meadowsweet, p. 3, Are there any interactions with medications?, http://rxlist.com/meadowsweet-page3/supplements.htm (2014).
stuartxchange.org, Philippine Medicinal Plants, Family Malvaceae, Okra, *Abelmoschus esculentus* (Linn.) Moench., http://www.stuartxchange.org/Okra.html (2014).
Ansari NM, Houlihan L, Hussain B, Pieroni A. Antioxidant activity of five vegetables traditionally consumed by south-Asian migrants in Bradford, Yorkshire, UK. Phytotherapy Research. Oct. 2005 19(10): 907-911.
Sturtevant EL. Sturtevant's Edible Plants of the World. U. P. Hedrick UP (ed). p. 343. http://www.swsbm.com/Ephemera/Sturtevants_Edible_Plants.pdf.
medicalhealthguide.com, Okra, http://medicalhealthguide.com/herb/okra.htm (2014).
Lengsfeld C, Titgemeyer F, Faller G, Hensel A. Glycosylated compounds from okra inhibit adhesion of Helicobacter pylori to human gastric mucosa. J Agric Food Chem. Mar. 24, 2004 52(6):1495-503. Abst.
Messing J, et al, Antiadhesive Properties of *Abelmoschus esculentus* (Okra) Immature Fruit Extract against Helicobacter pylori Adhesion. PLoS One 2014; 9(1):e84836. Published online Jan. 9, 2014.
Kumar R. et al, Evaluation of Abelmoschus Esculentus Mucilage as Suspending Agent in Paracetamol Suspension. Inter J Pharm Tech Research. Jul.-Sep. 2009 1(3): 658-665.
Natural Medicines, Eyebright, http://www.naturalstandard.com/databases/herbssupplements/eyebright.asp?#undefined. (2015).
Jeong HJ, Koo HN, Na HJ, Kim MS, Hong SH, Eom JW, Kim KS, Shin TY, Kim HM. Inhibition of TNF-alpha and IL-6 production by Aucubin through blockade of NF-kappaB activation RBL-2H3 mast cells. Cytokine. Jun. 7, 2002;18(5):252-9. (Abst).
Natural Medicines Comprehensive Database, Eyebright, http://naturaldatabase.therapeuticresearch.com/nd/Search.aspx?cs=&s=ND&pt=100&id=109&ds=. (2015).
botanical.com, A Modern Herbal, Mallows. http://www.botanical.com/botanical/mgmh/m/mallow07.html (2014).

(Continued)

*Primary Examiner* — Satyendra K Singh
(74) *Attorney, Agent, or Firm* — John R. Casperson

(57) ABSTRACT

A composition of matter useful for preventing or reducing the incidence of acid reflux comprises a mixture of meadowsweet herb extract, okra fruit powder, eyebright herb extract, marshmallow root extract, and *plantago asiatica* extract, in powdered form.

9 Claims, No Drawings

(56) References Cited

OTHER PUBLICATIONS

Blumenthalm, Busse WR, Goldberg A, Gruenwald J, Hall T, Riggins CW, Rister RS. The Complete German Commission E Monographs. Therapeutic Guide to Herbal Medicines. Am Botanical Council. Austin, TX 1998. p. 167.

Sutovska M, Nosalova G, Franova S, et al. The antitussive activity of polysaccharides from *Althaea officinalis* I., var. *Robusta*, *Arctium lappa* L., var. *Herkules*, and *Prunus persica* L. Batsch. Bratisl Lek Listy. 2007 108(2):93-9. (Abst).

Therapeutic Research, Great Plantain, http://rw.therapeuticresearch.com/nd/Search.aspx?cs=&s=ND&pt=100&id=677&ds=&name=Plantago+-asiatica+%28GREAT+PLANTAIN%29&searchid=46206969. (2015).

Blumenthal M, Busse WR, Goldberg A, Gruenwald J, Hall T, Riggins CW, Rister RS. The Complete German Commission E Monographs. Therapeutic Guide to Herbal Medicines. Am Botanical Council. Austin, TX 1998. p. 186.

Huang DF, Xie MY, Yin JY, Nie SP, Tang YF, Xie XM, Zhou C. Immunomodulatory activity of the seeds of *Plantago asiatica* L. J Ethnopharmacol. Jul. 30, 2009;124(3):493-8. doi: 10.1016/j.jep.2009.05.017. Epub May 23, 2009. (Abst).

Yin, Jun-Yi, Nie, Shao-Ping, Zhou, Chao, Wan, Yin, Xie, Ming-Yong. Chemical characteristics and antioxidant activities of polysaccharide purified from the seeds of *Plantago asiatica* L. J. Sci. Food Agric. Jan. 30, 2010 90(2):210-217. (Abst).

\* cited by examiner

CONTROL OF ACID REFLUX WITH BOTANICALS

FIELD OF THE INVENTION

One aspect of the invention relates to a method for preventing or at least reducing the frequency of acid reflux in humans. Another aspect of the invention relates to a composition of matter useful for preventing or reducing the frequency of acid reflux in humans. Another aspect of the invention relates to a method for treating Gastroesophageal reflux disease in humans. Another aspect of the invention relates to a composition of matter useful for treating gastroesophageal reflux disease in humans. Another aspect of the invention relates to alleviating the signs and symptoms of acid reflux in humans.

BACKGROUND OF THE INVENTION

The lower esophageal sphincter (LES) is a ring of muscle at the entrance to the stomach. If functioning normally, the LES closes as soon as food passes through it. With improper closure, acid produced by the stomach may move up into the esophagus. This may cause symptoms such as heartburn. If these symptoms happen at a frequency greater than twice a week, it is classified as acid reflux disease or gastroesophageal reflux disease (GERD).

Gastroesophageal reflux disease is common, occurring in 30-40% of adults in the USA. Current management is pharmacologically done with proton pump inhibitors. The use of proton pump inhibitors is known to result in maldigestion, causing incomplete (1) digestion of proteins by acid proteases, (2) incomplete or lack of solubilization essential minerals such as calcium and magnesium, (3) diarrhea caused by bacteria such as *Clostridium difficile*, (4) increased risk of bone fracture and (5) impaired absorption of vitamin B12.

OBJECTS OF THE INVENTION

It is an object of this invention to provide a composition that can be taken to prevent or reduce the frequency of acid reflux or heartburn.

It is another object of this invention to treat acid reflux disease without proton pump inhibitors.

It is a further object of this invention to treat acid reflux disease without impairing the digestion of proteins as a side effect.

It is another object of this invention to treat acid reflux disease without impairing the absorption of calcium, magnesium or vitamin B12.

It is another object of this invention to treat acid reflux disease without causing diarrhea in a significant percentage of patients.

It is another object of this invention to treat acid reflux disease without increasing the risk of bone fractures.

SUMMARY OF THE INVENTION

In one embodiment of the invention, there is provided a method for reducing the frequency of acid reflux incidents in humans. The method comprises identifying a human having pain associated with acid reflux during a trigger event selected from night or after a meal, and administering to said human a total amount in the range of 400 to 4800 mg of meadowsweet herb extract, okra fruit powder, eyebright herb extract, marshmallow root extract, and *Plantago asiatica* extract, prior to a trigger event, in powdered form.

In another embodiment of the invention, there is provided a composition of matter useful in the above method comprising a mixture of meadowsweet herb extract, okra fruit powder, eyebright herb extract, marshmallow root extract, and *Plantago asiatica* extract, in powdered form.

In another embodiment of the invention, the composition of matter is provided in the form an efficacious mixture comprising in the range of from about 10 wt % to 30 wt % meadowsweet herb extract; in the range of from about 10 wt % to 30 wt % okra fruit powder; in the range of from about 10 wt % to 30 wt % eyebright herb extract; in the range of from about 10 wt % to 30 wt % marshmallow root extract; and in the range of from about 10 wt % to 30 wt % *Plantago asiatica* extract, based on total weight of the composition.

In a preferred embodiment, the composition further comprises in the range of 1 wt % to 5 wt % of an enzyme to aid digestion.

When in capsule form, the composition can be taken on an as needed basis to prevent heartburn incidents, or on a daily basis to control acid reflux disease.

DETAILED DESCRIPTION OF THE INVENTION

We have developed a blend of botanicals for the prevention or at least management of acid reflux. The botanicals we used are taken from meadowsweet, okra, eyebright, marshmallow and *plantago* plants. For long term use, we recommend that the blend be used in combination with an enzyme to aid digestion, for example, pepsin.

For individuals that do not consume animal derived products, enzymes that digest proteins in an acid pH can be substituted. Suitable enzymes include those from (1) plants such as papain from the latex of *Carica papaya*, or bromelain isolated from the stem of pineapple, or ficin isolated from latex of figs; (2) fungal acid-stable proteases isolated from *Aspergillus oryzae*, *Aspergillus niger* or similar fungal sources; and (3) acid stable proteases from bacteria such as rennet. Preferred non-pepsin enzymes are papain and acid-stable fungal protease from *Aspergillus oryzae*.

Meadowsweet (*Filipendula ulmaria*) is a perennial herb in the Rosaceae family. It typically grows in damp meadows to a height of about four feet, and is noted for attracting wildlife. It contains tannins and salicin, a plant salicylate. It is recognized as possessing numerous medicinal properties, including stomachic, anti-rheumatic, as well as astringent and antacid properties. The medicinally applicable parts of meadowsweet are the above ground parts. The active ingredients include flavonoids, phenol glycosides and essential oil. It is not recommend for use where aspirin is contraindicated, such as in asmatics or children, nor with choline magnesium trisalicylate (Trilisate), nor with narcotic drugs, as it may potentiate narcotic effects.

Okra (*Abelmoschus esculentus*) is a flowering plant in the mallow family. The fruit is a food source. Okra fruit contains an abundant amount of pectin, mucilage, and starch. It is recognized as possessing antioxidant activity and is used in traditional African and Asian medicine as a mucilaginous food additive which functions as a protective agent against gastric irritation and inflammatory diseases. Studies have shown that okra extracts can block adhesion by *H. pylori*.

Eyebright (*Euphrasia officinalis*) is found in European meadows and contains a naturally high content of iridoid glycosides, including aucubin. Aucubin is known to have hepatoprotective properties and antimicrobial activity as well as to inhibit NF-kappaB activation in mast cells and reduce inflammation. It has been used orally for coughs, conjunctivitis, earaches, epilepsy, headaches, hoarseness, inflammation, jaundice, ophthalmia, rhinitis, skin ailments, sore throat and cancer.

Marshmallow (*Althaea officinalis*) is found in salt marshes, damp meadows, the sides of ditches, by the sea, and on the banks of tidal rivers. Marshmallow leaf and root are used orally for respiratory tract mucous membrane inflammation, dry cough, gastric mucosa inflammation, diarrhea, peptic ulcers, constipation, and urinary tract inflammation. Marshmallow contains polysaccharaides which have been shown to provide efficacious cough suppressing activity.

*Plantago asiatica* (Great Plantain) is used orally for cystitis with hematuria, bronchitis, colds, and for irritated or bleeding hemorrhoids. The chemical compounds in *Plantago asiatica* include mucilage, iridoid glycosides including aucubin and catapol, as well as tannin. *Plantago* is also known to have high vitamin K content. Due to its high vitamin K content, *Plantago* is not recommended in conjunction with Warfarin (Coumadin).

Good results can be achieved by combining the five botanicals in powdered form in amounts ranging from about ½ part to about two parts each by weight to form a mixture. A relatively smaller amount of enzyme can be used. For example pepsin (1:10,000 unit strength) can be combined in amounts ranging from about 5/100s parts to 20/100s part. On a weight percent basis, based on combined weight of the five active ingredients, the botanicals are each present in the composition an amount in the range of from about 10 wt % to about 30 wt %. The enzyme is present in an amount in the range of from about 1 wt % to about 5 wt % based on total weight of the composition.

Based on weight of meadowsweet herb extract, each part by weight of meadowsweet herb extract is taken with in the range of 0.5 to 2 parts by weight of okra fruit powder, in the range of 0.3 to 1.5 parts by weight of eyebright herb extract, in the range of 0.3 to 1.5 parts by weight of marshmallow root extract, and in the range of 0.3 to 1.5 parts by weight of *Plantago asiatica* extract, on a daily basis. An enzyme, for example, 1:10,000 unit strength pepsin, can be added in amounts in the range of 0.05 to 0.2 parts by weight.

In a specific embodiment, the blend is encapsulated and the composition of the product per capsule is a powdered mixture of (1) meadowsweet herb extract 100 mg, (2) okra fruit powder 100 mg, (3) eyebright herb extract 75 mg, (4) marshmallow root extract 75 mg, (5) *Plantago asiatica* extract 75 mg and (6) pepsin (1:10,000 units) 10 mg. Cellulose is used to fill the capsules to a standardized weight.

The Meadowsweet herb extract was a dry extract produced from European herb extracted at an extract ratio 3.5-4.5:1. The solvent extract used ethanol 30%/water 70%. The extract was procured from Naturex.

The Okra fruit powder obtained commercially from the air dried whole fruit of *Abelmoschus esculentus.*

The Eyebright herb extract was powder produced from extraction of whole herb, PE 4:1, extract solvent 50% ethanol/water 50%. The extract was procured from Naturex.

The marshmallow root extract was powder produced from the extraction of powdered root, extract PE 4:1, solvent system ethanol 10%/water 90%. The powder was procured from Naturex.

The *Plantago asicatia* extract was powder produced from seed extracted at PE 4:1; extract solvent 100% water. The powder was procured from Phytochem, International.

The Pepsin 1:10,000 is a proteolytic enzyme product resulting from processing hog stomach linings. The material is vacuum dried, freely soluble in water and practically insoluble in alcohol, chloroform and ether. Optimal ph range for activity in aqueous medium 3.0-4.5. One pepsin unit is defined as the quantity of enzyme that digests 10,000 times its weight of coagulated eff albumen under the conditions of the assay. In the product used there was 10 milligrams per capsule. Using the FCC definition, 10 mg of pepsin 1:10,000 would digest 100 grams of defined protein under laboratory conditions. The Pepsin used was a powder produced by American Laboratories, Inc.

The dilutent used was microcrystalline cellulose (MCC)

For patients needing treatment for persistent acid reflux, the initial treatment is 2-3 capsules taken twice daily, each capsule containing in the range of 200 to 800 mg of active ingredients, preferably 300 to 600 mg of active ingredients. In other words, the daily dose of active ingredients is in the range of 800 to 4800 mg daily, preferably divided, and more preferably in the range of 1200 to 3600 mg daily taken as two doses, conveniently in capsules containing a mixture of the active ingredients. After thirty days the number of capsules is reduced as needed to manage the reflux. However, it is expected that a dose of at least 400 mg of active ingredients will be needed to avoid incidents of acid reflux. Because of the interaction with the botanicals with some conditions or drugs, the use of the product for patients having asthma or using salicylates is not recommended.

The primary symptoms of dyspepsia include upper abdominal pain, belching, nausea, vomiting, abdominal bloating, early satiety, and abdominal distention (swelling). The combination of five herbs noted above, preferably along with an enzyme, for example pepsin to aid the degradation of food proteins, offers relief from dyspepsia, acid indigestion, sour stomach and heartburn.

In developing the invention, a number of products were clinically tried on patients to control the management of acid reflux that either did not work at all or only mildly reduced the management of pain associated with acid reflux such as "heart burn".

Two specific products on the market that are used to control these symptoms are Hi Pep manufactured by Medi Herb and Okra Pepsin $E_3$ sold by Standard Process.

Okra Pepsin $E_3$ contains dried okra fruit 100 mg, pepsin 1:10,000 20 mg and other botanical/animal extract for which weight claims are not made on the label. This product by itself was not clinically effective for control of the condition described.

The Hi Pep product contains 100 mg of meadowsweet herb 4:1 extract, 285 mg deglycyrrihizinzed licorice root 12:1 extract, 100 mg of chamomile flower 6:1 extract, and 5 mg of chamomile flower essential oil. This product used by itself was not clinically effective either for the condition described.

These products were then tried together for the management of the condition. When used together they failed to provide effective relief for the condition.

Other botanical combinations tested on patients included

A blend of marshmallow root powder extract PE 4:1 in combination with meadowsweet herb dry extract. This combination provided a minimal improvement of the condition.

A blend of eyebright herb extract in combination with *Plantago asiatica* seed PE 4:1. This combination also provided a minimal improvement of the condition.

Further, various blends of the ingredients described (meadowsweet extract, marshmallow extract, eyebright herb extract, *Plantago asiatica* seed extract, okra fruit powder and pepsin) were blended and then tested on patients. Up to 20 various blends were attempted but none were as efficacious as the specific blend described above to which 22 of 25 patients treated responded favorably, with no pain from reflux after using the product. Response to the product was as soon as 24 hours or within a few days. The clinical conditions that were commonly observed by these patients prior to treatment is that they were not in pain when they ate but had pain associated with reflux at night or after meals (trigger event).

The invention is further illustrated by the following case histories, in which the inventive capsules as described above as the specific embodiment are referred to as HCl-Ease.

Case History #1

Mr. J C age 56 presented himself on Mar. 13, 2014 with a chief complaint of "digestive issues" and reflux. The patient states having "bad digestion."

Past History:

The patient's past history consisted of chronic digestive issues, bloating pressure in the mid abdominal area, and reflux. Previous endoscopy revealed pre-Barrettes esophagus syndrome. Previous treatments included proton pump blocking agents and dietary changes i.e. reduction of spicy foods and coffee. Patient states these changes helped somewhat, but not enough to significantly reduce symptoms.

Treatment:

The Patient was placed on HCl-Ease at 3 BID and 1 methylfolate plus. A 4 week follow up was suggested.

Follow Up Visit Apr. 11, 2014

The patient states that all his GI tract symptoms have resolved. He also stated that he reduced the HCl-Ease to 2 BID and was still feeling very well. The patient is scheduled for a final visit in 8 weeks at which time there will be a discussion whether to continue the HCl-Ease at a low dose or discontinue.

Case History #2

On Nov. 21, 2013 Ms. A S presented herself to the office with a chief complaint of acid reflux. The patient refuses to take proton pump inhibitors or other types of "antacids". The acid reflux has been a complaint "on and off" in the past, but recently it has become consistent.

Past History

The patient has a previous history which includes depression, anxiety, hypertension and difficulty sleeping. She states that now these symptoms have become much less, but the acid reflux worsened.

Treatment

The patient was placed on HCl-Ease at 3BID for 2 weeks, and then lowered to 2BID. The patient called the office 2 weeks later to let us know that the acid reflux symptoms improved in 7 days and were completely resolved in 2 weeks.

$1^{st}$ Follow Up Visit Jan. 9, 2014

The patient returned with a complaint of fatigue. When asked about her reflux, she stated that she no longer had any stomach or intestinal problems.

$2^{nd}$ Follow Up Visit Jan. 24, 2014

The patient is generally feeling well. She hasn't used the HCL-Ease in the past 2 weeks, and has not used the HCl-Ease since her last visit.

Case History #3

Ms. A W, a 77 year old female with a history of inflammatory Colitis, returned for a follow up visit for her gastro intestinal condition. Previous treatment including dietary changes, pro-biotic GI tract permeability were prescribed by her gastroenterologist, there had positive effects.

Past History:

Several years of bouts of diarrhea and colitis with some epigastric discomfort. On Nov. 7, 2013 the patient returned back to the local hospital with a severe flare-up. Steroids were prescribed with only a minimal effect. The patient states having 4-5 bowel movements per day, all "very loose." The patient was prescribed HCl-Ease at 3 pills BID.

$1^{st}$ Follow Up Visit Nov. 25, 2013

The patient states that her symptoms are now up and down. The bowel frequency has lessened to only 2 bowel movements per day.

$2^{nd}$ Follow Visit Dec. 23, 2013

The patient states having about "a 50% improvement or a bit more" in her bowel movements.

$3^{rd}$ Follow Up Visit

The patient states feeling much better perhaps 80-90% better and wishes to stay on the HCl-Ease.

$4^{th}$ Follow Up Visit

No GI tract symptoms at all. Patient placed on a maintenance dose of HCl-Ease 2 BID, re-evaluation in 8 weeks.

Case History #4

Ms. J J, a 53 year old female presented herself on May 2, 2013 with a chief complaint of chronic reflux. Previous treatment included proton effect blocking medication, which had a positive effect.

Past History

The patient's previous history is unremarkable, other than left sacra-iliac joint pain which is made worse with horseback riding.

Treatment

The patient was placed on a general detoxification program with Bio-Cyanadins added to 3 BID.

$1^{st}$ Follow Up

The patient was greatly improved however some reflux symptoms remained.

$2^{nd}$ Follow Up on Dec. 17, 2013

The patient returned with severe reflux symptoms. Treatment at this visit consisted of HCl-Ease 3 BID.

$3^{rd}$ Follow Up Feb. 18, 2014

The patient returned for a follow up visit, she states that the pills helped quite a bit. There was only minor reflux when she drank coffee. At this visit the patient felt her reflux resolved enough, and wanted to begin treatment for her sacral-iliac joint pain.

Case History #5

Ms. E M, a 51 year old female presented herself on Aug. 23, 2011 with a chief complaint of "food sensitivities." Secondary complaints consisted of depression, anxiety, and gastric reflux. Currently not on any medication of GI complaints.

Past History

Bouts of gastritis related to food intake, mood issues, and reflux.

Treatment

Patient was placed on a food rotational diet to try to identify food sensitivities. Food allergy tests were inconclusive.

Follow Up Visits from Sep. 23, 2011 to Oct. 10, 2012

In the follow up visits it revealed an overall improvement in mood, however upper GI tract, nausea, and bouts of gastritis although less frequent were still an issue.

Follow Up Visit on Apr. 7, 2014

The patient states that the "pills" helped greatly, she no longer has symptoms of nausea or upper GI tract irritation. A follow up was suggested in 2 months to review continued use of the product.

Case History #6

Ms. C A, a 69 year old female presented herself on Dec. 6, 2013 with a chief complaint of nausea, with an "acidy stomach". Her upper GI tract complaint, which was intermittent in the past, has now become more severe and persistent.

Past History

The patient had presented herself to our office on Sep. 27, 2011 with billiary cirrhosis. Blood work performed on Feb. 18, 2011. All blood work was normal with exception of a slightly elevated ALT at 47. A follow up blood work up on Jul. 22, 2012 revealed an ALT of 150, an AST of 110 and an Alk Phos of 264, normal 38-126. At this time Phosphatidylcholine 2 BID was prescribed to stabilize the liver cell membrane.

Follow up blood work up on Aug. 10, 2011 revealed a normal ALT of 69 (just in range), an AST of 61 (normal 15-46). ALK Phos however increased to 307. Blackcurrant Seed Oil was added at 2 BID and Livotrit 2 BID. A follow up blood work up on Jan. 17, 2012 revealed a normal ALT of 37 and an AST of 52 (still elevated) and an ALK Phos of 91. The patient continued to improve on Jun. 14, 2012 a follow up blood work revealed an AST of 47 and an Alk Phos 132. On Sep. 17, 2013 a follow up blood work showed an increase of Alk Phos to 156 and AST of 49. The patient was placed on a genesis homeopathic to balance out the remainder of her biliary pathways.

Follow up blood work on Feb. 26, 2014 revealed a normal AST of 46 on a normal Alk Phos of 108. Throughout this time however the patient complained of nausea and acid reflux that did not improve.

Current treatment for gastric complaint: On Dec. 6, 2014 HCL ease was added to her treatment plan 3 BID. It should be noted that this was also the time when all her follow up tests improved. GGTP a more specific enzyme also was reduced from 159 to 140.

On Mar. 6, 2014 the patient stated that for the first time she was without nausea or reflux. She noted that the improvement she felt started after 10 days on HCl-Ease. It should also be noted that HCl-Ease had no negative effect on her liver enzymes, and in fact it may have helped lower them.

Case History #7

On May 9, 2013 Ms. I M presented herself with a chief complaint of upper gastric pain. She states that the pain began over 6 years ago. A current h-*pylori* breathe test was negative.

Past History

The patient states the she has had a long standing struggle with severe anxiety and associated depression. An endoscopy 2 years ago revealed a gastric ulcer and associated gastritis. The patient has tried proton blocking medication and hyoscononamine with only marginal improvement. Also the patient had her gallbladder removed 3 years ago.

Treatment

Her treatment began on May 9, 2013 with Gastrazyme prescribed at 3 BID. Also Beta plus 2 with each meal. It was also suggested that the patient eliminate all gluten.

$1^{st}$ Follow Up on Jul. 8, 2013

The visit revealed at least 80% improvement in all gastric symptoms.

$2^{nd}$ Follow Up Sep. 9, 2013

The visit revealed a mild relapse in symptoms. Other dietary changes are made.

$3^{rd}$ Follow Up Visit Oct. 14, 2013

The patient returned angry and in severe pain. She stated that even though she followed the treatment plan, the level of pain had become severe. Further questioning revealed that the patient had sulfite sensitivity. At that visit mo-zyme (molybdenum) was added at 1 BID.

$4^{th}$ Follow Up Visit Nov. 21, 2013

The patient states feeling approximately 40-50% better. At this visit HCl-Ease was added at 3 BID. The patient had such a significant reduction in symptoms that she called the office on Dec. 6, 2013 to state that she "loved the pills." For the first time in 6 years all the chronic pain had stopped.

$5^{th}$ Follow Up Visit on Jan. 13, 2014

She stated the only time she felt some "tightness" in her stomach was during bouts of severe anxiety. Current Patient is scheduled for a follow up on 5/2014

Case History #8

On Mar. 18, 2010 Mr. J M presented himself with severe reflux. The patient describes that after a meal if he bonds forward his "food will come up into his mouth." At night he has to sleep elevated, but still wakes up several times a night with "acid in my mouth." During the evening bouts the patient also complains of severe past nasal drip which compounds the problem.

Initial treatment consisted of a billiary Gall bladder detoxification treatment. This included Beta TCP at 3 BID, MCS 2 at 2 BID, Bio-Doph-7 at 2 before bed, and homeopathic $21^{st}$ century Detoxification number 1 at ½ capful BID.

During the course of the follow up visits from Apr. 21, 2010 through Nov. 30, 2010 the patient had marked improvement. However the evening reflux had not improved. Dietary changes had little or no effect.

On Nov. 19, 2013 the patient was placed on HCl-Ease at 3 before sleeping. The patient called the office 7 days later to state that he could now sleep through the night without reflux symptoms. It had been the first time in many years. The HCl-Ease worked best when taken in the evening. Also it should be noted that his post nasal drip was reduced by half during usage of the HCl-Ease before bed, and has not had any reoccurrence of symptoms.

Case History #9

On Oct. 17, 2013 Ms. M G, a 71 year old female presented herself with a chief complaint of acid reflux.

Past History

GI tract, intestinal bloating, and heart arrhythmias.

Treatment

The patient was placed on HCl-Ease at 3 BID, since the patient lived in Arizona; follow up visits consisted of phone consultations. On Dec. 30, 2013 the patient called to state that the HCl-Ease was working great. It completely eliminated her symptoms. It was suggested that she continue the HCl-Ease for 12 weeks, then discontinue, to see if symptoms return. To date she still remains symptom free.

Case History #10

On May 28, 2013 Ms. S P, a 50 year old female returned for a follow up visit. Previously the patient was treated on Aug. 3, 2010 for post Lyme's syndrome. On this visit she mentioned her problems related to her upper GI tract. They included bloating, nausea, and reflux. Then symptoms were worse in the evening. The symptoms had been progressing the past 3 months.

Treatment: Gastrazyme 3 BID and Intenzyme 2 TID.

$1^{st}$ Follow Up Visit

The patient states that her work schedule did not allow her the time for a follow up visit. Since the previous treatment did not help she had tried another practice or prescribed Betaine HCL. The pills greatly increased her symptoms after 2 weeks of the Betain HCl and said she was in debilitating pain. At this visit HCl-Ease was prescribed at 2 TID. The patient states that she felt improvement in 4-5 days and a complete recovery in 3 weeks.

2$^{nd}$ Follow Up Visit

On Jan. 3, 2014 she discontinued the HCl-Ease and still remains symptom free.

Case History #11

Ms. J H, a 22 year old female with a history of acid reflux presented herself with a complaint of occasional bad "heart burn."

Past History

Several years of acid reflux, the patient states that there is a family history of having acid reflux. Has had prescribed to her Prilosec for her reflux and states it "didn't help much."

Treatment

Patient was prescribed 2 BID of HCl-Ease. The patient states she doesn't get "heartburn too often." So I suggested taking HCl-Ease 20 minutes before a meal that would usually upset her stomach.

Patient states that she takes occasionally with certain foods and it helps prevent the acid reflux, or takes when the on-set of the acid reflux begins and dismisses the heart burn "in half hour or so." Patient is very pleased with the product and wishes to keep taking the supplement as needed Case History #12

Ms. P R, a 59 year old female presented with a chief complaint of C.O.P.D, asthma, emphysema, hypertension, acid reflux, and rheumatoid arthritis. She states that her breathing has progressively gotten worse.

Past History

Many years of poor lung capacity, patient also was a smoker but quit 14 years ago.

Current Medications:

Advair, Atorvastatin, Combivent, Respimat, Lisinopril, Singulair, Zoloft Nasonex, Proton blocking medication for reflux.

Initial Treatment

1. Mixed EFAs (omega 3, 6, 9 formula)
2. Bromelain Plus CLA
3. Saccharmycees boulardi 1st Follow Up Jul. 19, 2013

Breathing greatly improved generally more energy. Patient was left on her current protocol. Re-evaluation in 8 to 10 weeks.

2$^{nd}$ Follow Up Oct. 14, 2013

Patient states having mild set back for a couple of weeks, after having a head cold. Now during so well she is able to jog a bit. She states that she has been unable to do so for years.

Her treatment was to finish protocol and see if symptoms return. Patient called on Dec. 16, 2013 and wants to stay on original protocol. When she finished her treatment, her breathing was not quite as good.

3$^{rd}$ Follow Up Visit

Patient states that things are going very well. However she states that her acid reflux is severe, and the proton blocking medications isn't really helping much.

Treatment: HCl-Ease was added at 2-3 BID. 4$^{th}$ Follow up visit Patient states that the HCl-Ease completely eliminated her reflux symptoms. Patient will be re-evaluated in 3 months While certain preferred embodiments have been described herein, the invention is not to be construed as being so limited, except to the extent that such limitations are found in the claims.

What is claimed is:

1. A composition of matter formulated for oral administration, comprising a mixture of:
   in the range of from about 10 wt % to 30 wt % meadowsweet herb extract;
   in the range of from about 10 wt % to 30 wt % okra fruit powder;
   in the range of from about 10 wt % to 30 wt % eyebright herb extract;
   in the range of from about 10 wt % to 30 wt % marshmallow root extract;
   in the range of from about 10 wt % to 30 wt % *Plantago asiatica* extract, based on total weight of the composition; and
   in the range of 1 wt % to 5 wt % of an enzyme to aid in digestion of food.

2. The composition of matter according to claim 1, wherein the enzyme is pepsin.

3. The composition of matter according to claim 2 in capsule form and containing in the range of 200 to 800 mg combined weight of meadowsweet herb extract, okra fruit powder, eyebright herb extract, marshmallow root extract and *Plantago asiatica* extract.

4. A method for reducing the frequency of acid reflux incidents in humans, said method comprising;
   identifying a human having pain associated with acid reflux during a trigger event selected from night or after a meal, and
   administering orally to said human a total amount in the range of 400 to 4800 mg of the composition according to claim 1, prior to the trigger event, in powdered form.

5. The method according to claim 4, wherein in the range of 1200 to 3600 mg of the composition is administered to said human on a daily basis in divided doses together with the enzyme to aid in digestion of food.

6. The method according to claim 5, wherein the enzyme is pepsin.

7. A composition of matter formulated for oral administration, comprising a mixture of meadowsweet herb extract, okra fruit powder, eyebright herb extract, marshmallow root extract, and *Plantago asiatica* extract, in powdered form, wherein each part by weight of meadowsweet herb extract is accompanied by in the range of 0.5 to 2 parts by weight of okra fruit powder, in the range of 0.3 to 1.5 parts by weight of eyebright herb extract, in the range of 0.3 to 1.5 parts by weight of marshmallow root extract, in the range of 0.3 to 1.5 parts by weight of *Plantago asiatica* extract; and an enzyme to aid in digestion of food.

8. The composition of matter according to claim 7, wherein the enzyme comprises pepsin in the amount 0.05 to 0.2 parts by weight for each part by weight of meadowsweet herb extract.

9. A method for reducing the frequency of acid reflux incidents in humans, said method comprising;
   identifying a human having pain associated with acid reflux during a trigger event selected from night or after a meal, and
   administering orally to said human a total amount in the range of 400 to 4800 mg of the composition of matter according to claim 6 prior to the trigger event.

* * * * *